US008524502B2

(12) United States Patent
Basile et al.

(10) Patent No.: US 8,524,502 B2
(45) Date of Patent: Sep. 3, 2013

(54) APPARATUS AND METHODS FOR PERFORMING PHOTOREACTIONS AND ANALYTICAL METHODS AND DEVICES TO DETECT PHOTO-REACTING COMPOUNDS

(75) Inventors: Mark Basile, Hollis, NH (US); Anthony Jeannotte, Foxborough, MA (US)

(73) Assignee: Waters Technologies Corporation, Milford, MA (US)

( * ) Notice: Subject to any disclaimer, the term of this patent is extended or adjusted under 35 U.S.C. 154(b) by 123 days.

(21) Appl. No.: 12/989,210

(22) PCT Filed: Apr. 22, 2009

(86) PCT No.: PCT/US2009/041334
§ 371 (c)(1), (2), (4) Date: Dec. 9, 2010

(87) PCT Pub. No.: WO2009/134647
PCT Pub. Date: Nov. 5, 2009

(65) Prior Publication Data

US 2011/0263033 A1 Oct. 27, 2011

Related U.S. Application Data

(60) Provisional application No. 61/049,038, filed on Apr. 30, 2008.

(51) Int. Cl.

| | |
|---|---|
| ***G01N 33/00*** | (2006.01) |
| ***G01N 21/00*** | (2006.01) |
| ***B01J 19/12*** | (2006.01) |

(52) U.S. Cl.
USPC ............. 436/93; 436/161; 436/164; 436/165; 436/172; 436/174; 436/175; 422/70; 422/82.05; 422/82.08; 422/186.3; 204/157.6; 356/440; 356/442

(58) Field of Classification Search
USPC ............. 436/20, 93, 164, 165, 172, 161, 174, 436/175, 177, 178; 422/68.1, 70, 82.05, 422/82.08, 186.3; 204/157.6; 356/432, 436, 356/440, 441, 442
See application file for complete search history.

(56) References Cited

U.S. PATENT DOCUMENTS 3,647,387 A 3/1972 Benson et al.
4,181,853 A * 1/1980 Abu-Shumays et al. ...... 250/304

(Continued)

FOREIGN PATENT DOCUMENTS

GB 1570236 6/1980

OTHER PUBLICATIONS

Supplementary European Search Report, forms 1503, PO459, 1703 and 1507S, completion date May 17, 2011.

(Continued)

*Primary Examiner* — Maureen Wallenhorst
(74) *Attorney, Agent, or Firm* — Nielsen IP Law LLC

(57) ABSTRACT

The present invention is directed to devices and methods for performing photoreactions of photo-reacting compounds in solution. The invention features a vessel defining a chamber and a light source. The chamber has a chamber volume, a first window, an inlet and an outlet. The inlet is placed in fluid communication with a source of photo-reacting compounds in solution. The first window is transparent to light transmission and is placed in optical communication with a light source to receive photons. The chamber receives a solution of one or more photo-reactive compounds over time to define a dwell time. The device further includes a light source, in optical communication with the first window, for emitting photons which photons are received by the first window and transmitted into the chamber.

3 Claims, 14 Drawing Sheets

(56) References Cited

U.S. PATENT DOCUMENTS

| | | | | |
|---|---|---|---|---|
| 4,285,698 | A * | 8/1981 | Otto et al. | 436/20 |
| 4,656,141 | A | 4/1987 | Birks et al. | |
| 5,663,050 | A | 9/1997 | Bedell | |
| 5,866,074 | A | 2/1999 | Chapman et al. | |
| 6,503,719 | B2 | 1/2003 | Modlin et al. | |
| 2004/0108197 | A1 | 6/2004 | Buhr | |
| 2007/0172904 | A1 | 7/2007 | Dementieva et al. | |

OTHER PUBLICATIONS

Simeon, N., et al; "Some applications of near-ultraviolet laser-induced fluorescence detection in nanomolar- and subnnomolar-range high-performance liquid chromatography or micro-high-performance liquid chromatography"; Journal of Chromatography A. 913 (2001) 253-259.

Hershberger, L. W., et al; "Sub-Microliter Flow-Through Cuvette for Fluorescence Monitoring of High Performance Liquid Chromatographic Effluents"; Analytical Chemistry, vol. 51, No. 9, Aug. 1979.

Poulsen, James R. et al, Photoreduction Flourescence Detection of Quinones in High-Performance Liquid Chromatography, Analytical Chemistry, 1989, pp. 2267-2276, vol. 61, No. 20.

Huang, Jennifer et al, Analysis of Aflatoxins Using Fluorescence Detection, Thermo Scientific, Application Note:381, 2007.

Finnigan Surveyor FL Plus Detector, Flourescence Detector, Thermo Electron Corporation, Product Specifications, 2006.

Aflatoxins B & G, Picometrics, 2003, Application Note Reference AN 010-03A, HPLC-LIF 325 nm.

* cited by examiner

APPARATUS AND METHODS FOR PERFORMING PHOTOREACTIONS AND ANALYTICAL METHODS AND DEVICES TO DETECT PHOTO-REACTING COMPOUNDS

CROSS REFERENCE TO RELATED APPLICATIONS

This application is the National Stage of International Application No. PCT/US2009/41334, filed Apr. 22, 2009, which claims priority to and benefit of U.S. Provisional Patent Application Serial No. 61/049,038, filed Apr. 30, 2008. The entire contents of these applications are incorporated herein by reference.

STATEMENT REGARDING FEDERALLY SPONSORED RESEARCH OR DEVELOPMENT

None.

THE NAMES OF THE PARTIES TO A JOINT RESEARCH AGREEMENT

None.

REFERENCE TO SEQUENCE LISTING

None.

FIELD OF THE INVENTION

This invention relates to the field of photoreactions and, in particular, to analytical methods and devices to detect the presence or absence of aflatoxins.

BACKGROUND

This paper will use several terms and phrases in the manner defined below to facilitate an understanding of the invention. As used herein, the term "photoreaction" refers to a reaction in which one or more reactants form a product in the presence of photons. Several aflatoxins are photoreactive in the presence of water, co-reactive solvents or other participants in photo-reactions and photons. Aflatoxins are naturally occurring toxins produced by fungi. Some aflatoxins produce characteristic fluorescence at certain wavelengths. Some of the photoreaction products of aflatoxins also produce fluorescence.

As the name suggests, aflatoxins are toxic to humans and most animals. Foodstuffs and animal feeds are routinely tested; however, the tests are time consuming and reagent intensive.

It would be desirable to have devices and methods which can identify aflatoxins in samples. As used herein, the term "sample" is used broadly to mean a material to be tested. In the context of aflatoxins, such samples are typically a tissue, food, processed or unprocessed material which is used in food or pharmaceutical processing, preparation and manufacturing, and materials taken from solid surfaces or fluids by means of wipes, swabs or fluid aliquots.

SUMMARY OF THE INVENTION

The present invention is directed to devices and methods for performing photoreactions. The methods and devices of the present invention have particular application in the testing of samples for the presence of aflatoxins. One embodiment of the present invention, is directed to a device, for performing photoreactions of photo-reacting compounds in solution, has the following major elements: a vessel and a light source. The vessel has at least one wall defining a chamber. The chamber, for performing photoreactions, has a chamber volume, a first window, an inlet and an outlet. The inlet is for being placed in fluid communication with a source of photo-reacting compounds in solution. The outlet is for discharging products of the photoreaction. The first window is transparent to light transmission and is placed in optical communication with a light source to receive photons. The chamber is for receiving a solution over time to define a dwell time. The solution potentially has one or more photo-reactive compounds having a concentration. The device further comprises a light source, in optical communication with the first window, for emitting photons which photons are received by the first window and transmitted into the chamber. The light source emits photons at an excitation wavelength and has an intensity to place at least 5 to 50,000 photons in the solution for each photo-reacting compound molecule traveling through the chamber at a concentration of $1.0\times10^{-13}$ to $1.0\times10^{-6}$ moles per liter to form product.

As used herein, the term "product" refers to the product of the photoreaction caused by the interaction of the photons with the reactants.

A preferred light source has a flux of at least $1.0\times10^{15}$ to $1.0\times10^{17}$ photons per second and produces photons having a wavelength of approximately 365 nanometers, or 241 nanometers or 313 nanometers. These wavelengths are efficiently received by aflatoxins with approximately 365 nanometers being the most preferred. A preferred aflatoxin is selected from the group consisting of P1, Q1, M1, B1, G1, B2, and G2. A preferred light source is a laser or lamp such as a mercury xenon lamp or light emitting diode.

Preferably, the chamber is constructed and arranged to cooperate with the source of sample to have a dwell time in the range of 0.25 to 20 seconds per chamber volume. And, more preferred, the dwell time is 0.25 to 2.0 chamber volume per second. The inlet, preferably, receives a solution having as much as $4.0\times10^{-6}$ moles per liter.

One preferred device comprises a source of solutions potentially containing one or more photo-reacting compounds. A preferred source is a chromatography system which system is capable of separating photo-reactive compounds from each other and other non-photo-reactive compounds. One preferred chromatographic system comprises a liquid chromatograph pump equipped with a column. The chromatographic column receives a sample potentially comprising one or more aflatoxins and separates each aflatoxin from each other and other compounds.

Preferably, the chamber has a second window in optical communication with a fluorescent detector. The fluorescent detector is capable of detecting one or more products in the event said photo-reacting compound is present in solution. A preferred detector is a monochromator. The photo-reaction products of several aflatoxins are fluorescent upon excitation with light of wavelength approximately 365 nanometers at an emission wavelength of between 420 and 460 nanometers for aflatoxin B1 reaction products and 445 to 465 for aflatoxin G1 reaction products.

A further embodiment of the present invention is directed to a method for performing photoreactions of photo-reacting compounds in solution. The method comprises the steps of providing a device having a vessel and a light source. The vessel has at least one wall defining a chamber, for performing photoreactions. The chamber defines a chamber volume and has a first window, an inlet and an outlet. The inlet is for being placed in fluid communication with a source of photo-reacting compounds in solution. The outlet is for discharging products of the photoreaction. The window is transparent to transmission of photons and is placed in optical communication with a light source to receive photons. The chamber receives a solution over time to define a dwell time. The solution has or potentially has a concentration of molecules of photo-reacting compounds. The light source is in optical communication with the window and emits photons which photons are received by said window and transmitted into the chamber. The light source emits photons at an excitation wavelength and having an intensity to place at least 5 to 50,000 photons in the solution for each photo-reacting compound molecule traveling through the chamber at a concentration of $1.0\times10^{-13}$ to $1.0\times10^{-6}$ moles per liter to form product. And, the method comprises the step of directing a solution containing photo-reacting compounds or potentially containing photo-reacting compounds into the chamber as said light source directs photons therein to form a product.

The light source preferably has a flux of at least $1.0\times10^{15}$ to $1.0\times10^{17}$ photons per second. The chamber preferably has a dwell time of 0.25 to 20 seconds per chamber volume. The method can process a solution having $4.0\times10^{-6}$ moles of photo-reactant compounds per liter efficiently. This small number of photo-reactive compounds is preferably detected by fluorescent detection devices. For example, without limitation, embodiments of the present invention are used to detect the presence or absence of one or more afflatoxins, including, aflatoxins selected from the group consisting of M1, B1, G1, B2, and G2. These aflatoxins are detected at low concentrations, such that the detection has significant health safety benefits. These aflatoxins are detected at low concentrations without further derivitization and modification other than the photo-reactions.

Preferably, the source of photo-reacting compounds in solution is a liquid chromatographic column. The chromatographic column receives a sample potentially comprising one or more aflatoxins and separates each aflatoxin from each other and other compounds.

Preferably, the chamber has a second window in optical communication with a fluorescent detector, such as a monochromator. The fluorescent detector detects one or more products in the event a photo-reacting compound is present in solution. Thus, a preferred method comprises the step of monitoring the detector for a signal indicative of the presence of one or more photo-reactive compounds. The absence of a signal is indicative of the absence of the photo-reactive compounds.

These and other features and advantages will be apparent to those skilled in the art upon viewing the drawings and reading the detailed description that follows.

DETAILED DESCRIPTION OF THE INVENTION

The present invention is directed to devices and methods for performing photoreactions. The methods and devices of the present invention have particular application in the testing of samples for the presence or absence of aflatoxins with the understanding that embodiments of the present invention have utility for performing photoreactions without detection and for compounds other than aflatoxins.

Figure 1:
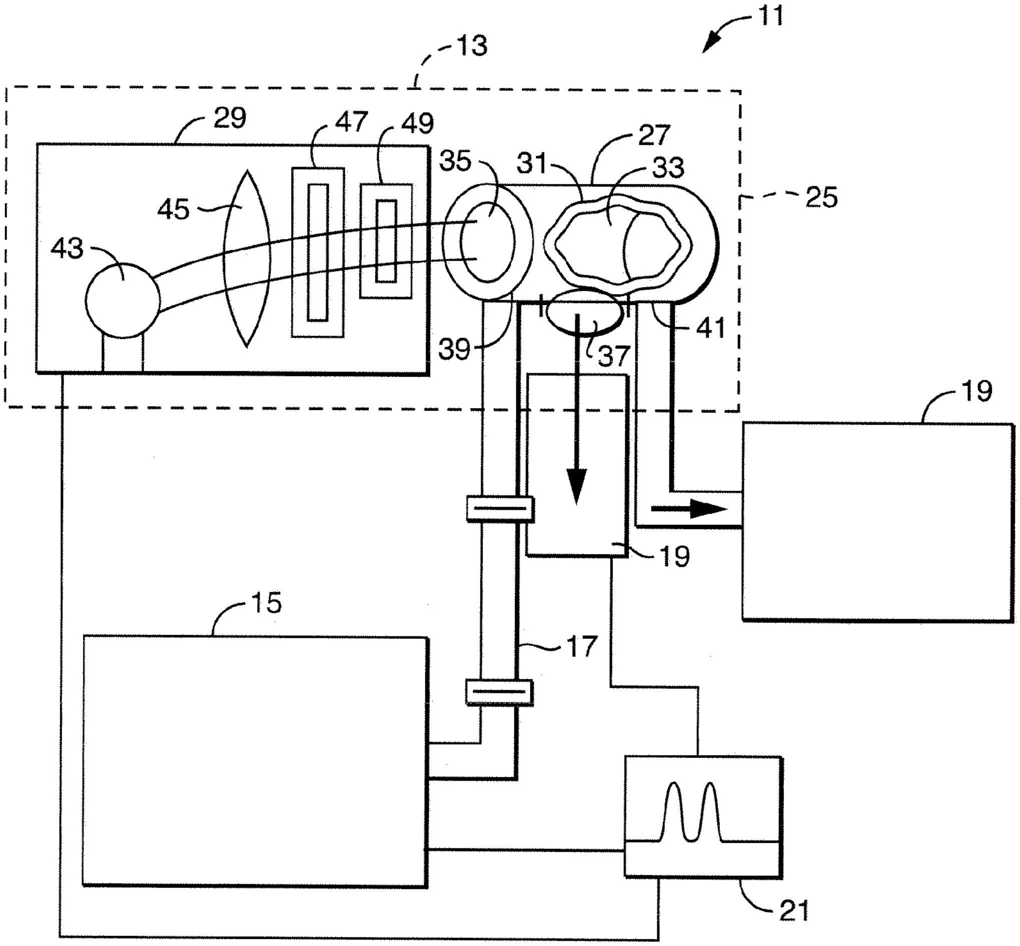
FIG. 1 depicts an apparatus embodying features of the present invention.

Turning now to FIG. 1, a device, for performing photoreactions of photo-reacting compounds in solution, generally designated by the numeral 11 is depicted. The device 11 has the following major elements: a reaction assembly 13, a chromatographic system 15 equipped with a solid phase separation device 17, a fluorescence detector 19 and control means 21.

The reaction assembly 13 comprises housing 25, a vessel 27 and a light source 29. The housing 25, depicted in schematic form, is a structure to contain the vessel 27 and light source 29. Housings of the type depicted are known in the art and are typically metal box-like assemblies which provide a protective cover and means of securing the vessel 27 and light source 29 in working relationship to each other.

The vessel 27 is depicted in partial cutaway and has at least one wall 31 defining a chamber 33. Chamber 33 is for performing photoreactions and has a chamber volume, a first window 35 a second window 37, an inlet 39 and an outlet 41. The vessel 27 is made of metal, such as titanium, steel, stainless steel, brass, aluminum, metal alloys, and other rigid structural materials, such as, by way of example, glass or plastic. The wall 31 may be coated with material such as amorphous fluorocarbon polymers with refractive indices less than the solutions which are to be contained in the chamber 33 such that photons are not absorbed by the wall 31. In such cases provided the angular range of the light beam directed into chamber 33 is correctly chosen, the efficiency of photoreactions may be enhanced through light guiding effects. A preferred fluorocarbon polymer is sold under the trademark TEFLON AF® (Dupont, Wilminton, Del.).

The chamber volume is preferably constructed and arranged to cooperate with the source of sample, for example the chromatographic system 15, to have a dwell time of 0.25 to 20 seconds per chamber volume. For example, without limitation, chamber 33 has a generally rectangular shape with a length of approximately 5.0 millimeters and a cross-section of approximately 1.60×1.60 millimeters. The total volume is, preferably 12.8 microliters. These dimensions and volumes are consistent with a flow cell sold in association with a ALLIANCE® chromatography system (Waters Corporation, Milford, Mass.).

First window 35 is transparent to light transmissions at desired wavelengths and is in optical communication with light source 29. For example, first window 35 can be made of fused silica.

A preferred light source is a laser or light emitting diode [not shown] or lamp system depicted. The lamp system which comprises the light source 29 has a lamp 43, focusing element 45, wavelength selecting element, such as grating 47 and slit 49. Those skilled in the art will recognize that in the event the light source is a laser light emitting diode such laser would be selected, tuned or set to emit at a desired wavelength as described more fully below. And, of course, the laser would comprise supporting power sources and controls.

As depicted, the focusing element 45 is shown as a lens, however, it is more conventional to use mirrors [not shown] as a focusing element to collect light and focus such light on the grating 47. The grating 47 diffracts light into wavelengths such that a particular wavelength can, in combination with other focusing elements [not shown], be directed at the slit 49. The grating 47 may be substituted with a prism [not shown] which performs the same function yet may be less efficient. The slit 49 is depicted as part of the light source 29; however, the slit 49 may also be integral to the first window 35. A preferred lamp 43 is a mercury xenon lamp.

The light source 29 emits photons at an excitation wavelength. Mercury xenon lamps have strong emissions at the excitation wavelength for aflatoxins. The wavelength is set by adjusting the grating 47 and slit 49 or in the case of a laser, or light emitting diode selecting or tuning the laser to a particular wavelength. The radiant output from light source 29 has an intensity to place at least 5 to 50,000 photons in the solution for each photo-reacting compound molecule traveling through the chamber at a concentration of $1.0\times10^{-13}$ to $1.0\times10^{-6}$ moles per liter to form product. A preferred concentration is approximately $1.0\times10^{-10}$ moles per liter.

A preferred light source 29 has a flux of at least $1.0\times10^{15}$ to $1.0\times10^{17}$ photons per second. With respect to aflatoxins, photons having a wavelength selected from the group of 365 nanometers, or 241 nanometers or 313 nanometers are preferred. These wavelengths are efficiently absorbed by aflatoxins, with 365 nanometers being the most preferred.

A preferred aflatoxin is selected from the group consisting of M1, B1, G1, B2, and G2. These aflatoxins are depicted in the formulas 1-5 set forth below:

Formula 1

M1

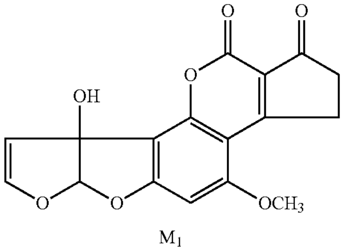

$M_1$

-continued

Formula 2

B1

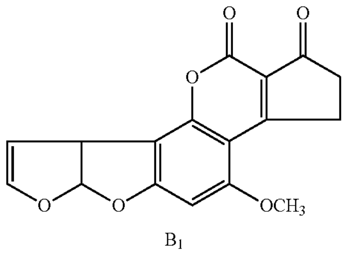

$B_1$

Formula 3

G1

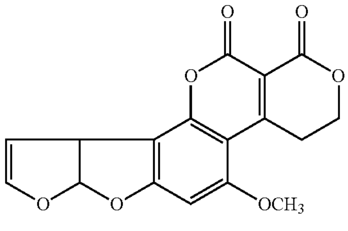

$G_1$

Formula 4

B2

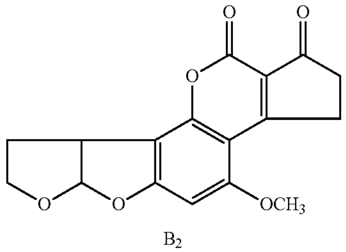

$B_2$

Formula 5

G2

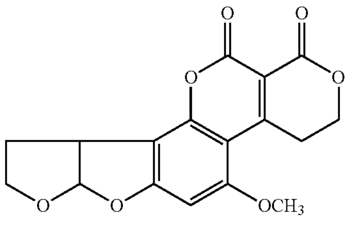

$G_2$

These aflatoxins and in particular B1 and G1 undergo photo-assisted reactions across the double bond in the furan ring. This reaction is described in reaction equation 1 set forth below:

Reaction Equation 1

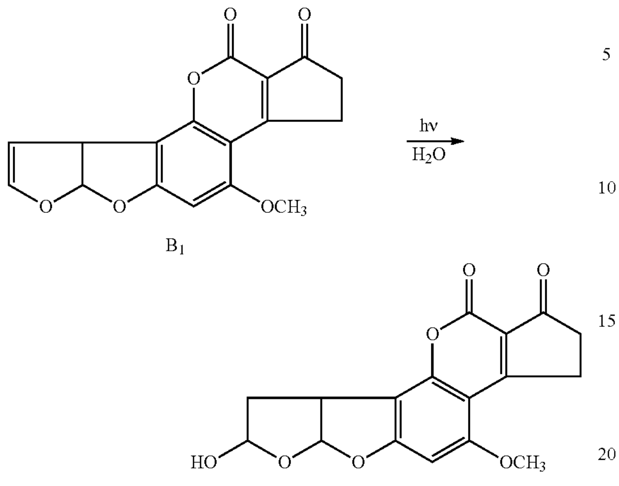

$B_1$ $B_{2A}$

Embodiments of the present invention allow detection of aflatoxins at low concentrations without additional steps of chemically modifying the aflatoxins in separate reaction vessels.

The inlet 39 is for being placed in fluid communication with a source of photo-reacting compounds in solution. The inlet 39, preferably, receives a solution having as much as $4.0\times10^{-6}$ moles per liter and directing such solution into the chamber 33.

A preferred source is chromatography system 15 and equipped with a solid phase extraction device, such as column 17. As used in the context of this application the term "column" is intended to encompass all solid phase extraction devices including monolith separation devices, packed bed devices, cartridges and wells. The chromatography system 15 and column 17 separates photo-reactive compounds from each other and other non-photo-reactive compounds. Chromatography systems 15 and columns 17 are well known in the art and are available from several venders; for example, the ALLIANCE® and ACQUITY® chromatography systems and OASIS®, ACQUITY HPLC®, XBRIDGE™, ATLANTIS®, XTERRA™ and SYMMETRY® columns (Waters Corporation, Milford, Mass.).

The outlet 41 is for discharging products of the photoreaction. Thus, the outlet 41 is typically in fluid communication with a receptacle [not shown] or one or more additional detectors. For example, without limitation the outlet may be connected to one or more detectors, such as a mass spectrometer or additional monochromator [not shown], or a sampling system such as a fraction collector overseen by control system 21 whereby peaks eluting through chamber 33 are captured into discrete sample vials for further analysis.

Second window 37 receives photons produced by fluorescence from the aflatoxins and or product of the photo-reactions. Second window 37 is made of fused silica in the manner of first window 35. The quantity of photons corresponding to the fluorescent light is normally a small fraction of the light entering the chamber 33 from first window 35, and second window 37 is preferably set ninety degrees with respect to the light path of such entering light.

Second window 37 is in optical communication with fluorescent detector 19. The photo-reaction products of several aflatoxins are fluorescent at an excitation wavelength of approximately 365 nanometers and an emission wavelength of between 420 and 460 nanometers for aflatoxin B1 reaction products and 445 to 465 nm for aflatoxin G1 reaction products. The fluorescent detector 19 has features of a monochromator. These features, known in the art, have been omitted from the drawing for the purpose of clarity as to other details. Those skilled in the art would understand that the fluorescent detector would comprise a means for separating wavelengths of light such as a grating or prism and a photodetector. The grating or prism would be tuned to wavelengths known to be emitted by the analyte.

The signal from the fluorescent detector 19 is received by control means 21. Control means 21 is a data management system comprising one or more computer processing units (CPU). CPUs are well known in the art and are available from numerous vendors. CPU comprising the control means 21 may be embedded in the chromatographic system 15 or held in separate computer devices, such as main frame computers, servers, personal computing devices, laptop computers and the like. The signal from fluorescent detector 19 is processed by the control means 21 and compared to values associated with aflatoxins. Signals which are above threshold values associated with aflatoxins are presumed to be positive for the presence of aflatoxins and signals below such values are presumed to be negative. These data are printed or displayed on a screen.

Control means 21 is depicted as in signal communication with chromatography system 15 and light source 29. In the event a change in the excitation wavelengths of the light source 29 or the emission wavelengths is desired, the control means 21 issues commands to effect such changes. Control means 21 commands chromatographic system 15 to determine injection times, flow rates, solvents and gradients.

One embodiment of the present invention directed to a method for performing photoreactions of photo-reacting compounds in solution will now be described with respect to the operation of device 11. The method comprises the steps of providing a device 11 having a vessel 27 and a light source 29. The vessel 27 has at least one wall 31 defining a chamber 33, for performing photoreactions. The chamber 33 defines a chamber volume and has a first window 35, a second window 37, an inlet 39 and an outlet 41. The inlet 39 is in fluid communication with a source of photo-reacting compounds in solution, chromatographic system 15 and column 17. The outlet 41 is for discharging products of the photoreaction.

The first window 35 is transparent to transmission of photons and is placed in optical communication with a light source 29 to receive photons. The chamber 33 receives a solution over time to define a dwell time. The solution has or potentially has a concentration of molecules of photo-reacting compounds. The light source 29 emits photons which photons are received by the first window 35 and transmitted into the chamber 33. The light source 29 emits photons at an excitation wavelength and having an intensity to place at least 5 to 50,000 photons in the solution for each photo-reacting compound molecule traveling through the chamber at a concentration of $1.0\times10^{-13}$ to $1.0\times10^{-6}$ moles per liter to form product.

And, the method comprises the step of directing a solution containing photo-reacting compounds or potentially containing photo-reacting compounds into the chamber 33 as said light source 29 directs photons therein to form a product and monitoring the emissions from second window 37 for fluorescence with a fluorescence detector 19.

These features and advantages are further described with respect to the following Examples.

EXAMPLE 1

Optimum Excitation and Emission Wavelengths of Aflatoxin Analysis

The excitation wavelength was 365 nm set in light source 29 for all five of the aflatoxins in this work. The 365 nm excitation wavelength coincides with the strong mercury emission line from the Hg—Xe lamp. The emission wavelength was 456 nm for the G and 434 nm for the B and M aflatoxins. These wavelengths were chosen based upon excitation and emission scans of solutions of G1 and B1.

Figure 3:
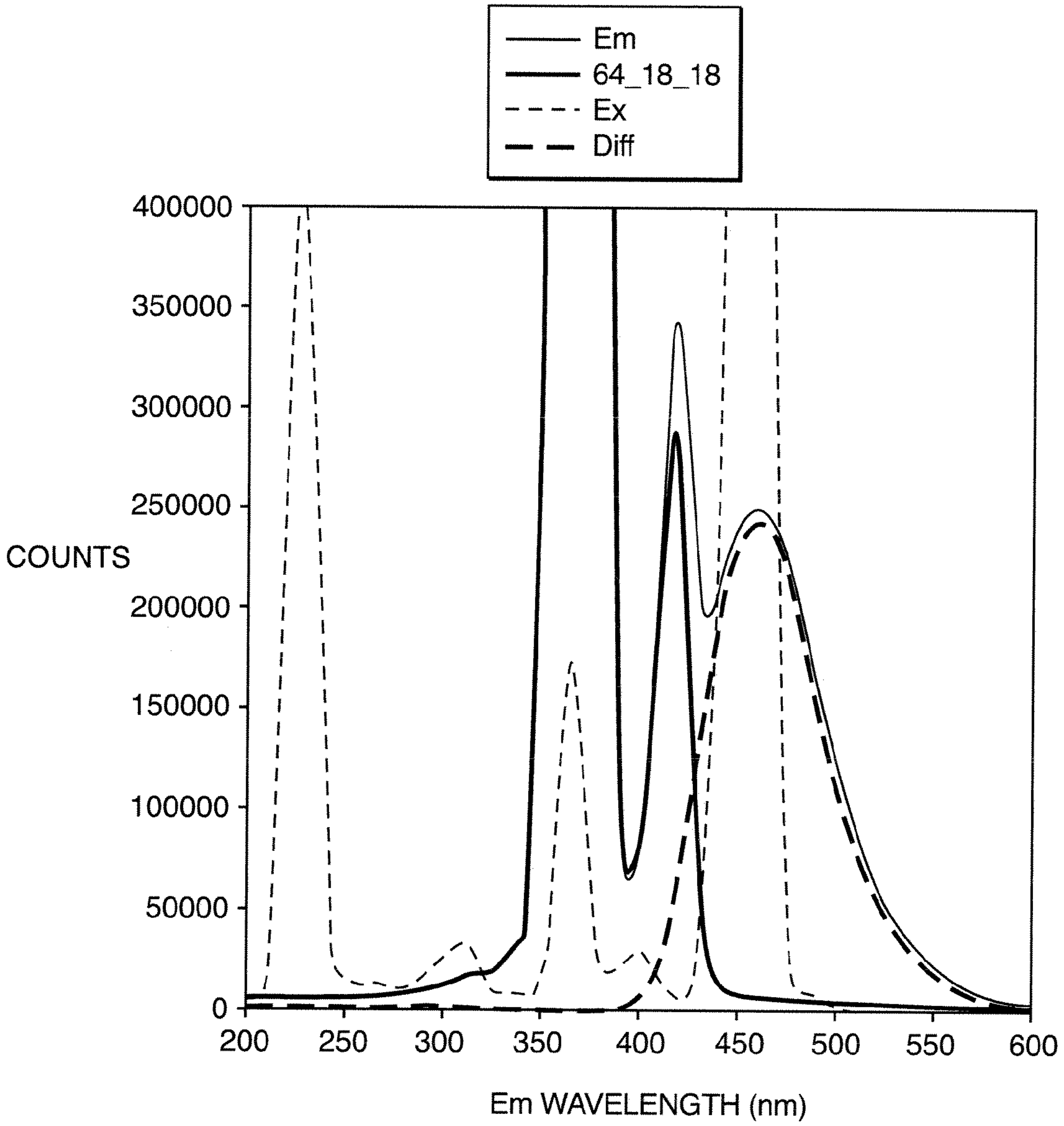
FIGS. 3 and 4 are the emission and excitation spectra for 1 ppb solutions of G1 and B1 aflatoxins along with the baseline emission spectra for the 64/18/18 solvent mixture of water/methanol/acetonitrile.
Figure 4:
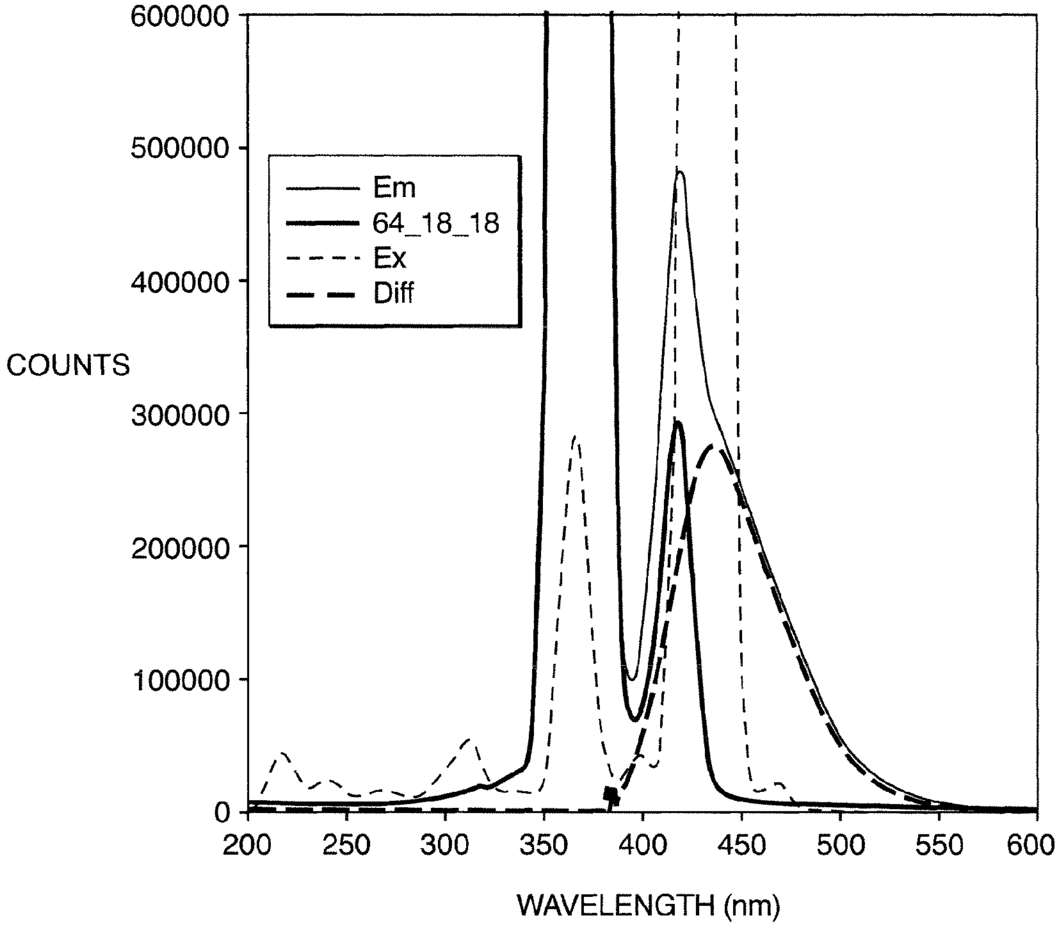
Figure 5:
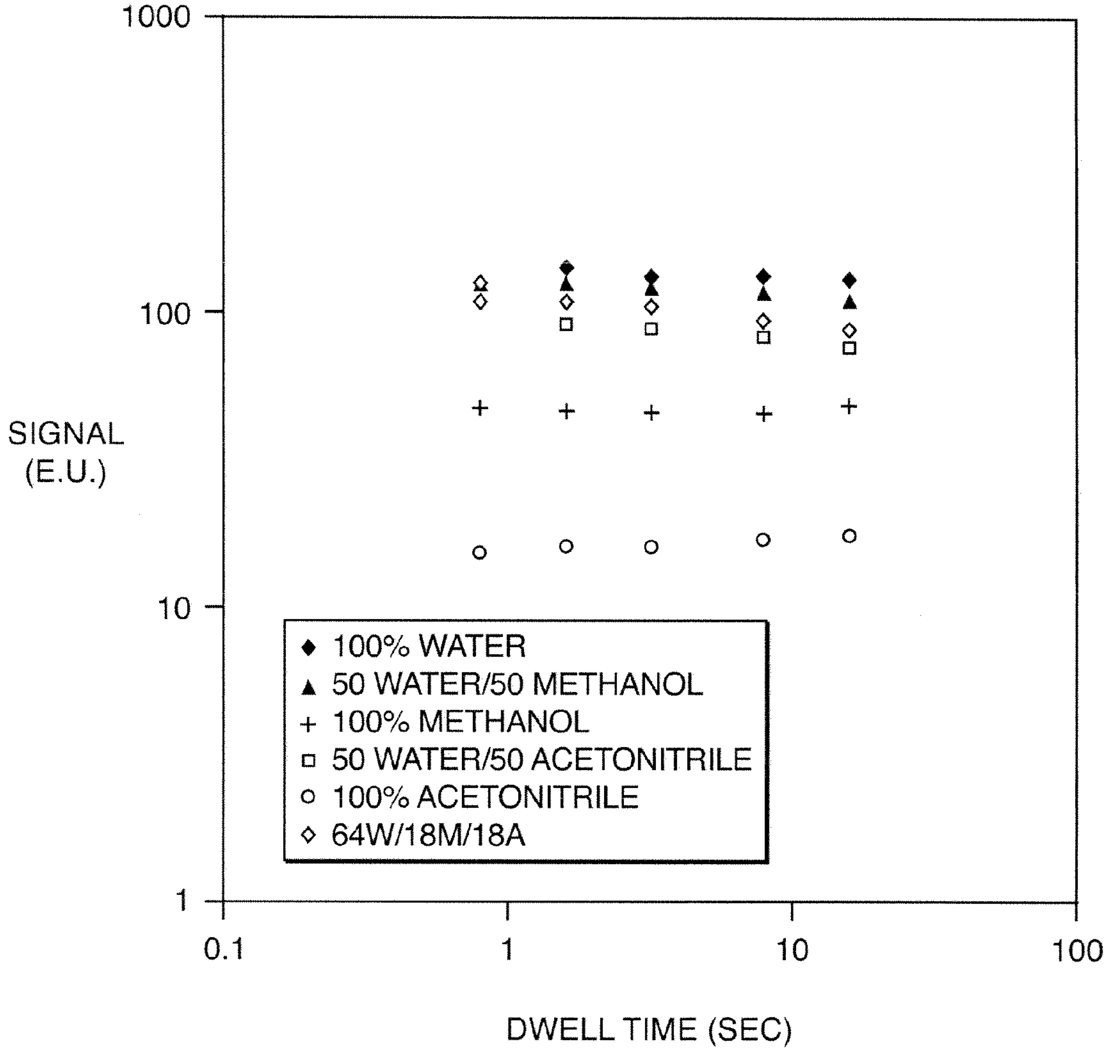
FIG. 5 depicts signal versus dwell time for M1 aflatoxin in an apparatus embodying features of the present invention.
Figure 6:
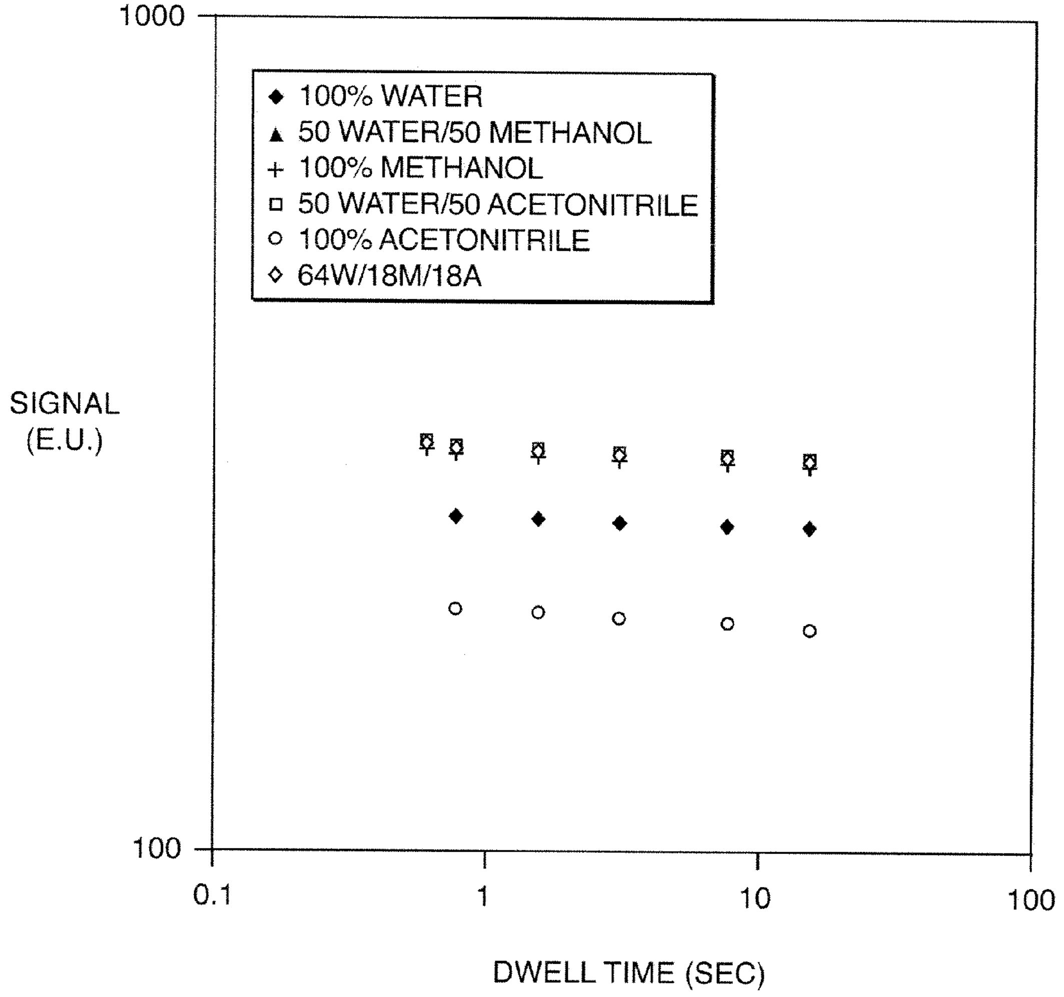
FIG. 6 depicts signal versus dwell time for G2 aflatoxin in an apparatus embodying features of the present invention.
Figure 7:
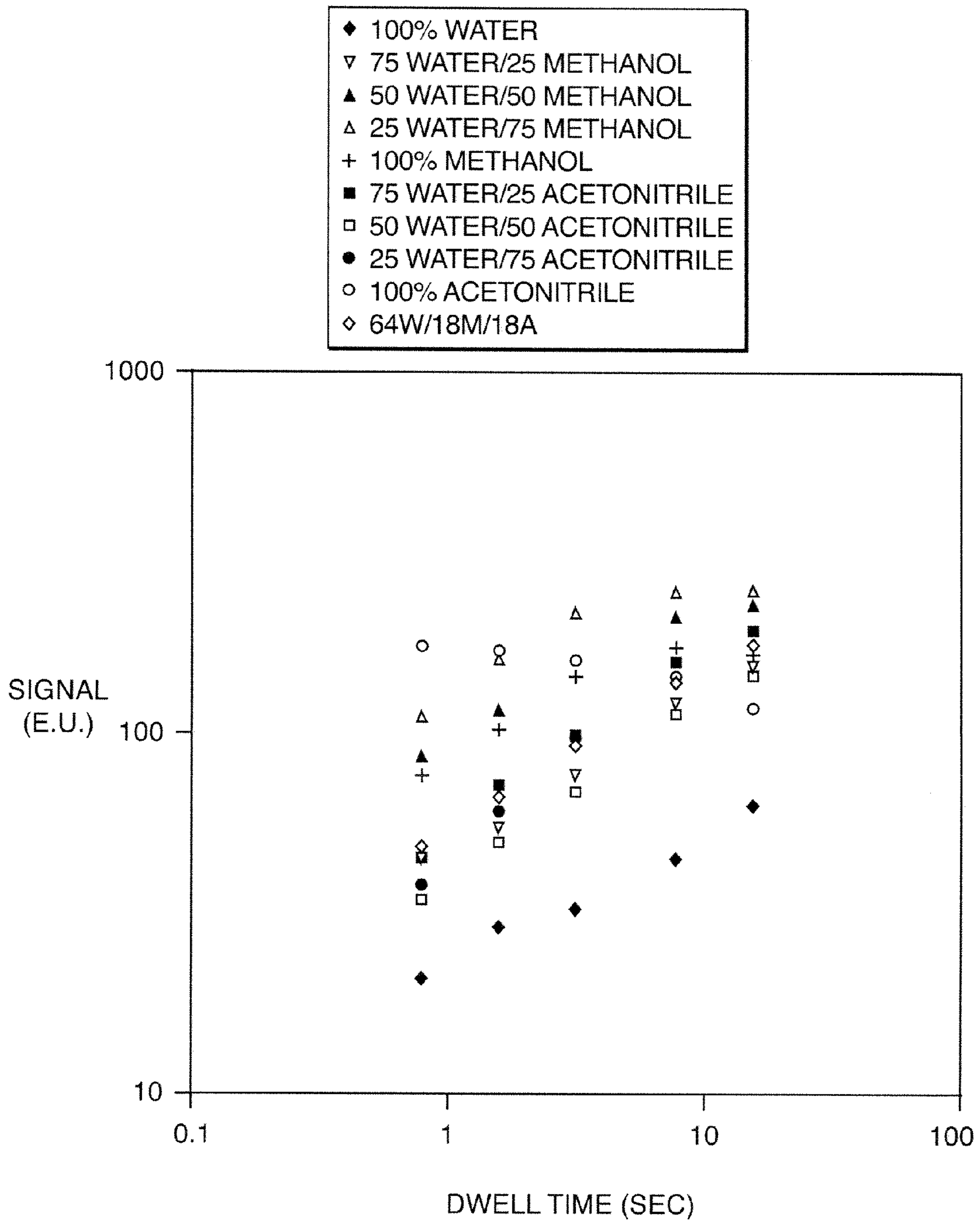
FIG. 7 depicts signal versus dwell time for G1 aflatoxin in an apparatus embodying features of the present invention.
Figure 8:
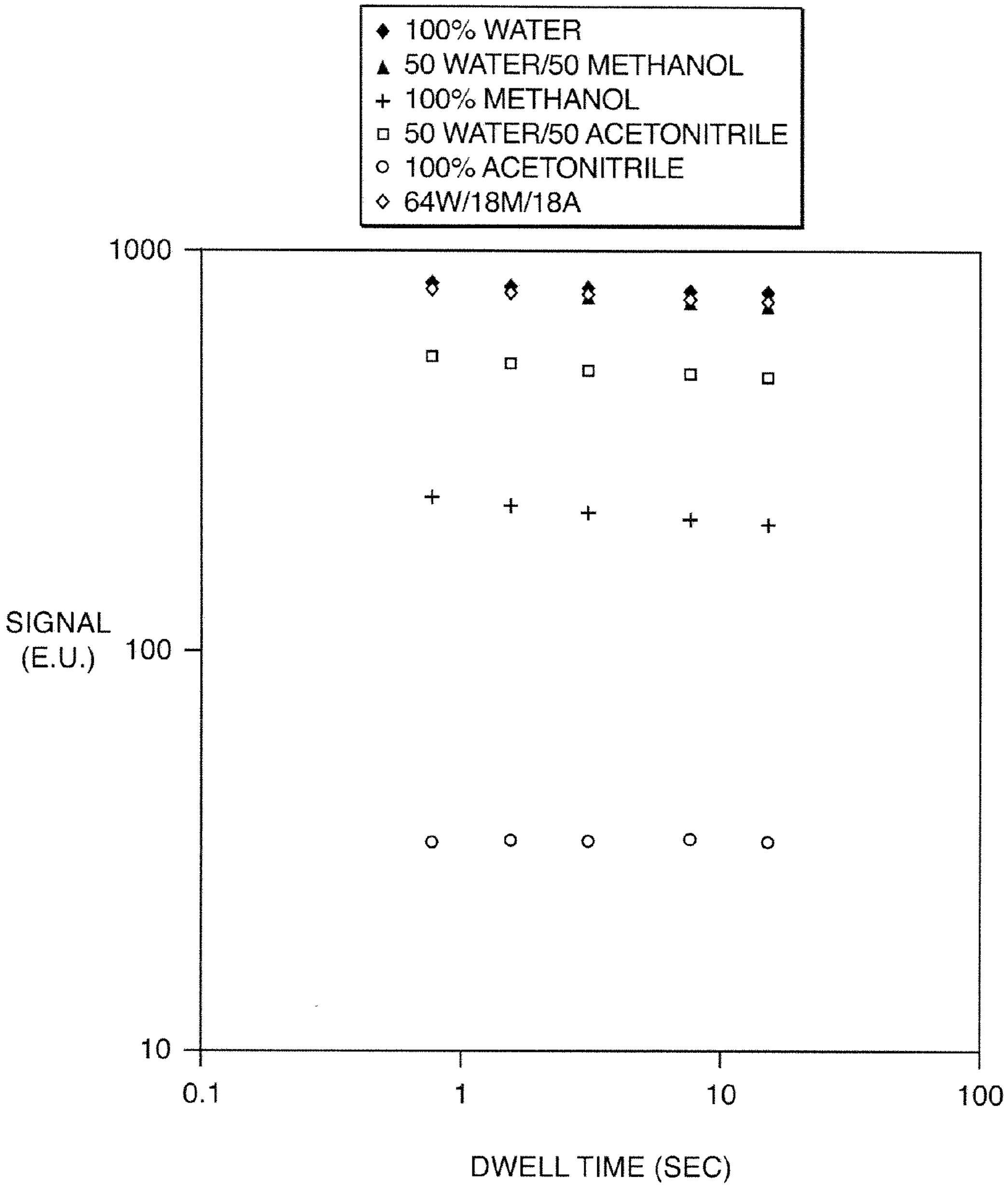
FIG. 8 depicts signal versus dwell time for B2 aflatoxin in an apparatus embodying features of the present invention.
Figure 9:
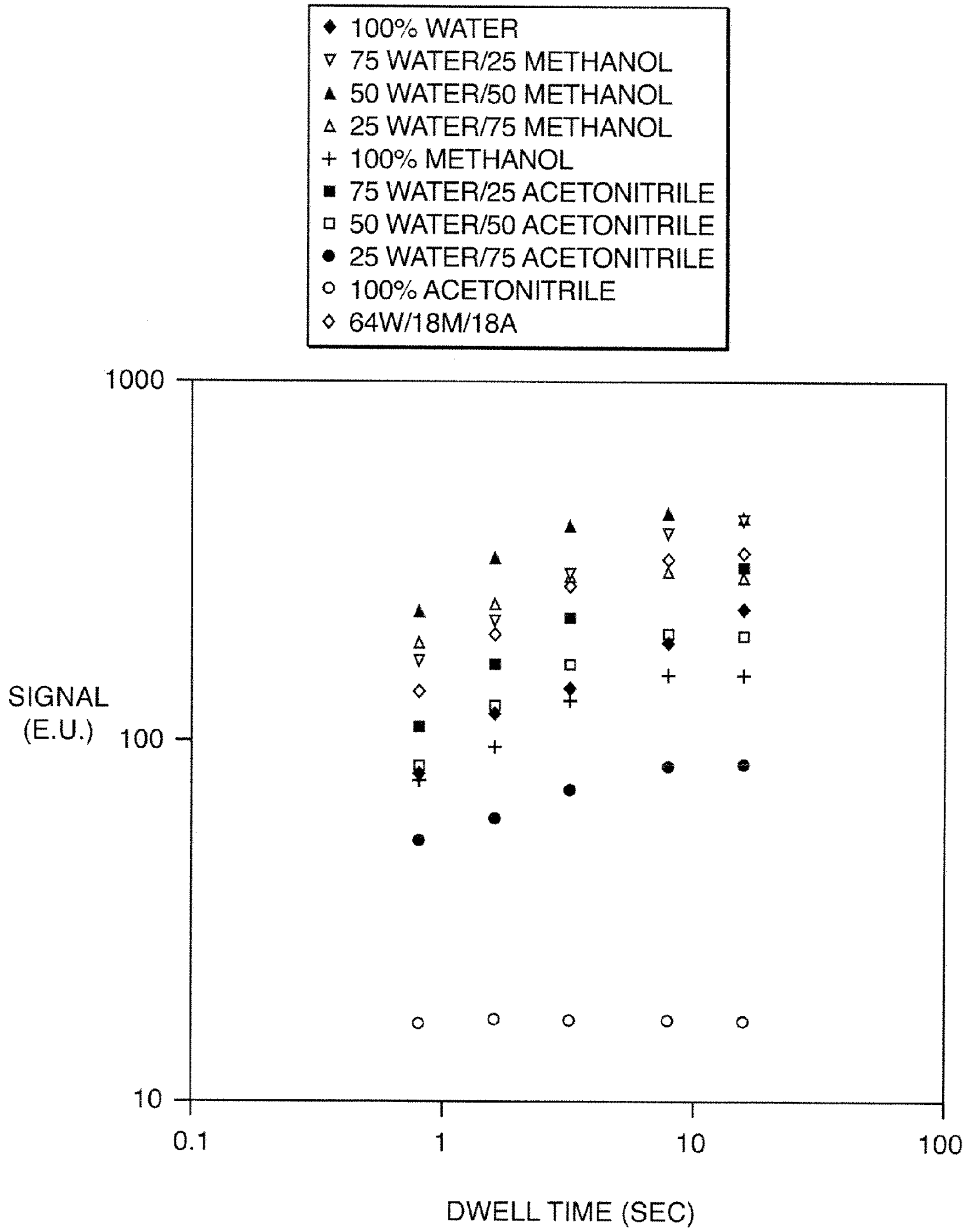
FIG. 9 depicts signal versus dwell time for B1 aflatoxin in an apparatus embodying features of the present invention.

FIGS. 3 and 4 depict the emission and excitation spectra for 1 ppb solutions of G1 and B1 aflatoxins along with the baseline emission spectra for the 64/18/18 solvent mixture of water/methanol/acetonitrile at the stated conditions. FIG. 3 depicts the C1 aflatoxin with emission and excitation scans. The Diff curve is the difference between the Em spectra and the 64/18/18 baseline spectra. The difference is the emission spectra of the aflatoxin. The excitation curves are included to show 365 nm excitation wavelength is the best choice for this system.

The G1 excitation curve has peaks at 228 nm, 313 nm, 365 nm, 405 nm and 456 nm. The peak at 228 nm is excitation light scattered into the emission monochromator and seen as second order at 456 nm and is not indicative of fluorescence. The peak at 456 nm is scattered excitation light seen by the emission system and again is not indicative of fluorescence. The peaks at 313 nm, 365 nm and 405 nm are from excited fluorescence and the peak at 365 nm is clearly several times larger than the other peaks and so is the best excitation wavelength from the Hg—Xe source. Turning now to FIG. 4, the B1 excitation curve has significant peaks at 217 nm, 313 nm, 365 nm, 405 nm and 434 nm. The peak at 217 nm is excitation light scattered into the emission monochromator and seen as second order at 434 nm and is not indicative of fluorescence. The peak at 434 nm is scattered excitation light seen by the emission system and again is not indicative of fluorescence. The peaks at 313 nm, 365 nm and 405 nm are from excited fluorescence and the peak at 365 nm is again several times larger than the other peaks and so is the best excitation wavelength from the Hg—Xe light source 29.

EXAMPLE 2

Residence or Dwell Time Studies

A study was undertaken on the effect of residence time of the aflatoxins in the chamber 33. Since photoreactions depend on the number of photons encountering the molecules and the output of lamp 43 is fixed, the molecules can be exposed to more photons as they flow through the chamber 33 by lowering the flowrate. The effect of the solvent mixture composition was also evaluated. The method presently uses a 64/18/18 mixture of water/methanol/acetonitrile. Table 1 shows the solvent compositions tested for each of the aflatoxins.

The flow rate was step changed during the running of a given aflatoxin in a given solvent composition. Flow rates used were 1, 0.5, 0.25, 0.1 and 0.05 ml/minute. The fluorescence signal was monitored at the different flow rates for each aflatoxin and solvent composition.

Figure 2:
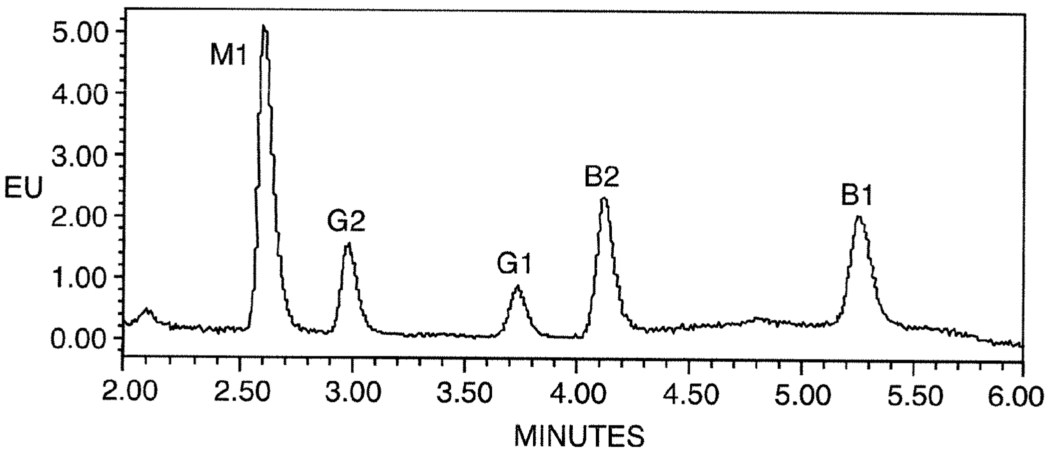
FIG. 2 is a chromatogram of aflatoxins made by an device embodying features of the present invention.

The results for 1 ppb solutions of the aflatoxins in the various solvent compositions are presented in FIGS. 5 through 9 in the order of elution as shown in the chromatogram of FIG. 2. The data is presented as a plot of fluorescence signal (ordinate) versus residence or dwell time (abscissa). Residence time is calculated as chamber volume divided by flowrate. The slope of the curve in the linear portion is indicative of the reaction rate.

The non or weakly photoreactive aflatoxins (M1, G2 and B2) were seen to have relatively flat to slightly negative responses to residence time in all the solvent compositions tested.

The G1 aflatoxin was most fluorescent in pure acetonitrile at the shortest residence time, but the fluorescence decreased with increasing residence time in the pure acetonitrile and fell below the signals measured in some of the other solvent mixtures at residence times over 1.56 seconds. All of the other solvent compositions showed a trend of increasing signal with increased residence time. The curves which display an eventual leveling off of signal with prolonged residence time are understood to represent species that have photoreacted as completely as possible in the flowcell conditions (not necessarily full conversion).

The B1 aflatoxin displayed the trend of increasing signal with increasing residence time except in acetonitrile which displayed a flat response in signal to residence time. The B1 aflatoxin also showed a leveling off of signal in some solvent mixtures with longer residence times.

Figure 10:
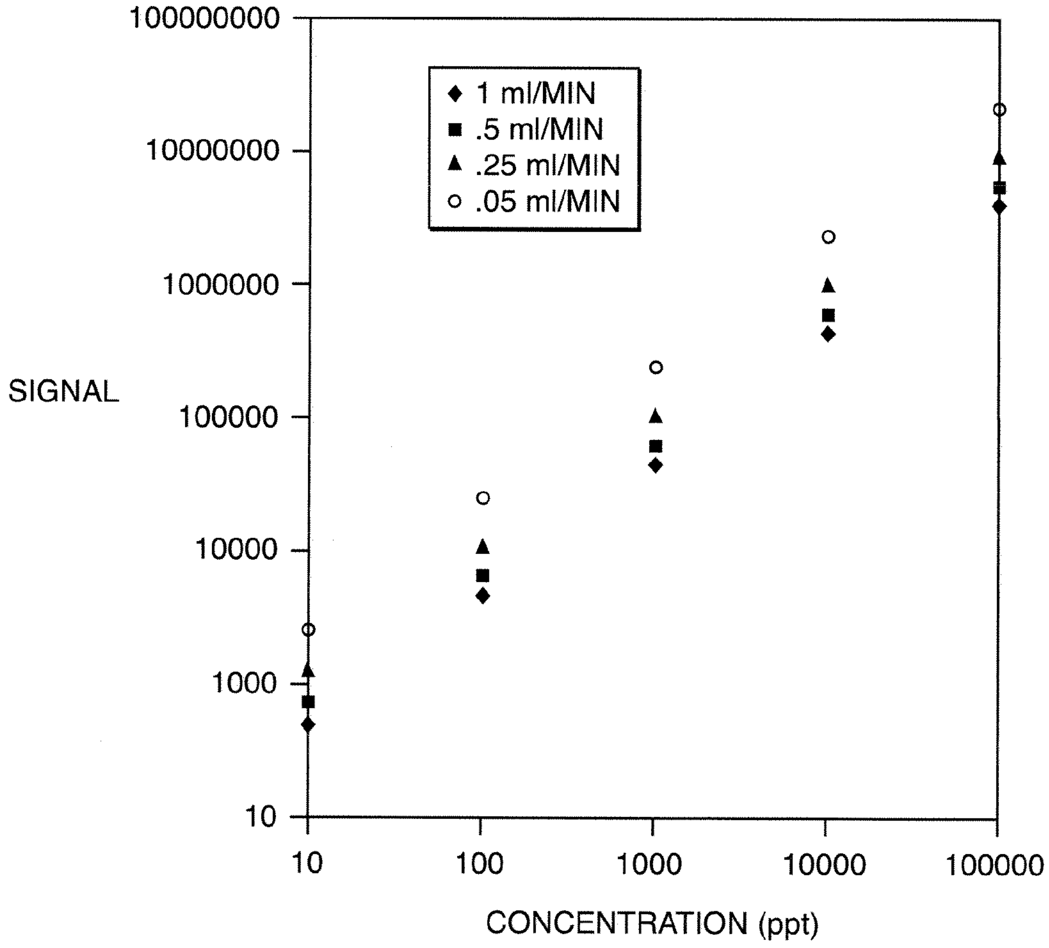
FIG. 10 depicts signal versus concentration for G1 aflatoxin in an apparatus embodying features of the present invention.
Figure 11:
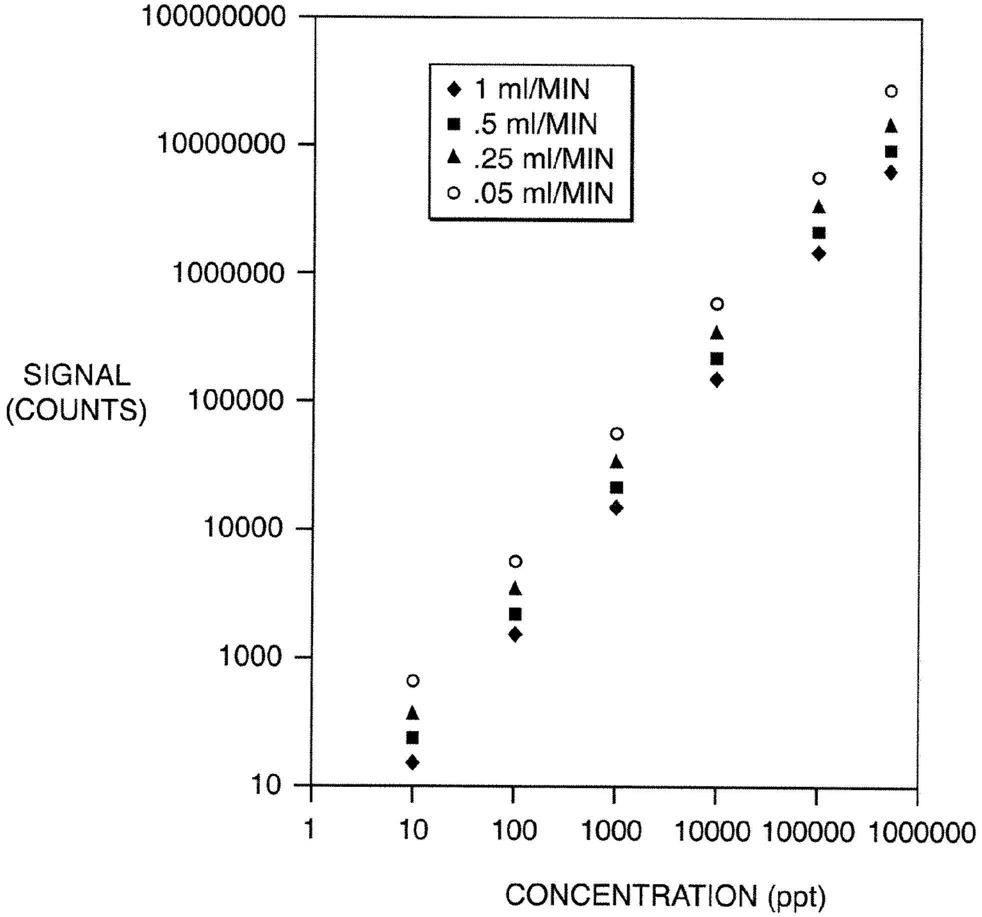
FIG. 11 depicts signal versus concentration for B1 aflatoxin in an apparatus embodying features of the present invention.

A separate series of runs over a broad range of concentrations was made in the 64/18/18 mobile phase with G1 and B1 aflatoxins to evaluate if the photoreaction occurred over a large range of concentrations. Results for these solutions are shown in FIGS. 10 and 11. The experiment showed good linearity over the range evaluated. The relationship between instrument response, here measured in so-called Emission Units or EU's, and analyte concentration is established through a calibration step preceding the overall chromatographic measurement. This calibration step is known in the art, routinely performed and compensates for changes in instrumental properties such as decreasing output of lamp 43 or optical transmission characteristics of various components within light source 29, vessel 27 or detector 19.

Changing the emission wavelength for the B aflatoxins to 450 nm from the 434 nm may improve detection sensitivity. The background levels would be reduced by 4 to 5×, by moving the emission wavelength further away from the solvent Raman emission. The shift to 450 nm only drops the aflatoxin fluorescence signal to about 80% of peak value. This shifting of emission wavelength could yield a 2× improvement in baseline noise and nearly the same in improved S/N performance.

TABLE 1

Solvent Compositions Run for Aflatoxins

| Solvent Composition | M1 | G2 | G1 | B2 | B1 |
|---|---|---|---|---|---|
| 100% water | X | x | x | x | x |
| 75/25 water/methanol | | | x | | x |
| 50/50 water/methanol | X | x | x | x | x |
| 25/75 water/methanol | | | x | | x |
| 100% methanol | X | x | x | x | x |
| 75/25 water/acetonitrile | | | x | | x |
| 50/50 water/acetonitrile | X | x | x | x | x |
| 75/25 water/acetonitrile | | | x | | x |
| 100% acetonitrile | X | x | x | x | x |
| 64/18/18 water/methanol/acetonitrile | X | x | x | x | x |

EXAMPLE 3

Wavelength Effect on Photoconversion and Signal

This example involved the passing of a constant composition solution of an aflatoxin through two detectors in series.

In the first detector, the excitation wavelength was changed between 241 m, 313 nm, 365 nm and 405 nm. A light-shuttering mechanism was interposed between the light source 29 and first window 35. With the shutter in the 'open' position, the excitation light was allowed to pass into chamber 33; photons were prevented from reaching the solution in the 'closed' position.

Figure 12:
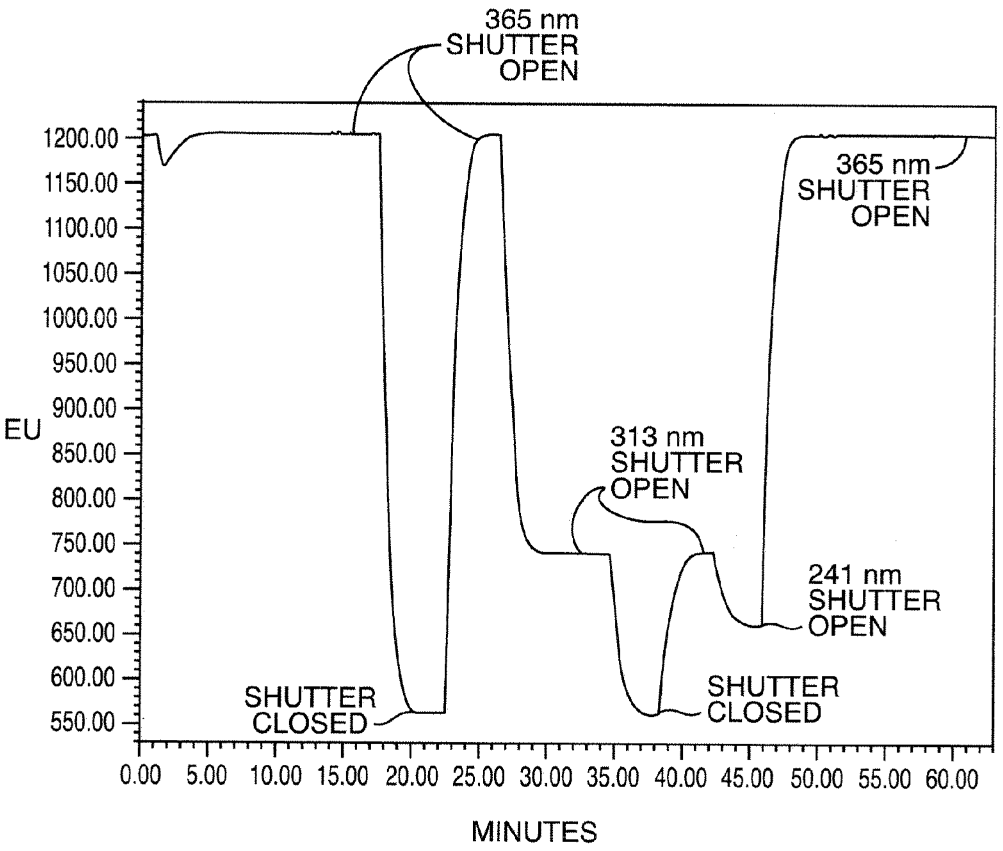
FIG. 12 depicts signal from the fluorescent detector at various wavelengths.

A second fluorescent detector [not shown] was used to monitor the outflow from chamber 33. This detector employed an excitation wavelength of 365 nm and emission wavelengths of 434 nm for B1 and 456 nm for G1 solutions. Typical results are presented in Table 3 below; an example of one of the runs, 100 ppb G1 at 0.5 ml/minute, used to generate this data is shown in FIG. 12. It may be seen in FIG. 12 that the signal with the shutter open is always greater than that with it closed which indicates a photochemical enhancement taking place within chamber 33. Further, the enhancement is greatest when the wavelength of photons entering chamber 33 is around 365 nm.

TABLE 3

| Solution | Flowrate (ml/min) | Residence time (sec) | wavelength(nm) | shutter position | FLR Signal (E.U.) |
|---|---|---|---|---|---|
| 1 ppb G1 | 1 | .78 | 365 nm | open | 19.6 |
| 1 ppb G1 | .5 | 1.56 | 365 nm | open | 30.3 |
| 1 ppb G1 | .25 | 3.12 | 365 nm | open | 44 |
| 1 ppb G1 | .1 | 7.8 | 365 nm | open | 65 |
| 1 ppb G1 | 1 | .78 | none | closed | 8.5 |
| 1 ppb G1 | .5 | 1.56 | none | closed | 10.3 |
| 1 ppb G1 | 1 | .78 | 313 nm | open | 11.4 |
| 1 ppb G1 | 1 | .78 | none | closed | 8.5 |
| 1 ppb G1 | 1 | .78 | 241 nm | open | 10.1 |
| 1 ppb G1 | 1 | .78 | none | closed | 8.5 |
| 1 ppb G1 | .5 | 1.56 | 405 nm | open | 11.3 |
| 1 ppb G1 | .5 | 1.56 | none | closed | 10.3 |
| 100 ppb G1 | .5 | 1.56 | 365 nm | open | 1206 |
| 100 ppb G1 | .5 | 1.56 | none | closed | 563 |
| 100 ppb G1 | .5 | 1.56 | 313 nm | open | 742 |
| 100 ppb G1 | .5 | 1.56 | None | closed | 563 |
| 100 ppb G1 | .5 | 1.56 | 241 nm | open | 663 |
| 100 ppb G1 | .5 | 1.56 | none | closed | 563 |
| 1 ppb B1 | .5 | 1.56 | 365 nm | open | 74 |
| 1 ppb B1 | .5 | 1.56 | none | closed | 23.1 |
| 100 ppb B1 | .5 | 1.56 | 365 nm | open | 2175 |
| 100 ppb B1 | .5 | 1.56 | none | closed | 503 |
| 100 ppb B1 | .5 | 1.56 | 313 nm | open | 1141 |
| 100 ppb B1 | .5 | 1.56 | none | closed | 503 |
| 100 ppb B1 | .5 | 1.56 | 405 nm | open | 520 |
| 100 ppb B1 | .5 | 1.56 | none | closed | 503 |
| 100 ppb B1 | .5 | 1.56 | 241 nm | open | 820 |
| 100 ppb B1 | .5 | 1.56 | none | closed | 503 |

An efficiency for each wavelength expressed in units of EU/photon is calculated as (Signal with shutter open-Signal with shutter closed)/(photons/sec/residence time flowcell). The calculated efficiency factors for these runs are given below in Table 4 where now the factors are normalized to the efficiency factor associated with the excitation wavelength of 365 nm at a particular flow rate and composition; these normalized efficiencies are referred to as 'Fraction' in this table.

TABLE 4

Efficiency factors and conditions for experimental setup

| Wavelength (nm) | Solution | Flowrate (ml/min) | Residence time(sec) | Fraction |
|---|---|---|---|---|
| 365 | 1 ppb G1 | 1 | .78 | 1 |
| 313 | 1 ppb G1 | 1 | .78 | .25 |
| 241 | 1 ppb G1 | 1 | .78 | .57 |
| 365 | 1 ppb G1 | .5 | 1.56 | 1 |
| 405 | 1 ppb G1 | .5 | 1.56 | .20 |
| 365 | 100 ppb G1 | .5 | 1.56 | 1 |
| 313 | 100 ppb G1 | .5 | 1.56 | .27 |
| 241 | 100 ppb G1 | .5 | 1.56 | .71 |
| 365 | 100 ppb B1 | .5 | 1.56 | 1 |
| 313 | 100 ppb B1 | .5 | 1.56 | .36 |
| 241 | 100 ppb B1 | .5 | 1.56 | .76 |
| 405 | 100 ppb B1 | .5 | 1.56 | .004 |

The efficiency factors show 365 nm to be the most efficient wavelength followed by 241 and 313 nm. The lamps output into the flowcell at 241 m is about 3.2 e15 photons per second versus about 1.3 e16 photons per second at 313 and 365 nm. The result of the slighter lower efficiency at 241 nm along with roughly a fourth of the photon flux results in significantly lower FLR signals at 241 nm.

EXAMPLE 4

Mass Spectrometry and Chromatography of Photoreaction Products

Samples of photoreaction product were generated by flowing a constant composition solution of 100 ppb of either B1 or G1 aflatoxin in the standard 64/18/18 solvent mixture through chamber 33 at a flowrate of 0.5 ml/min. The excitation wavelength was set at 365 nm for generating these samples. Samples exposed in this way were collected at the outlet 41 then injected as a sample for chromatographic separation using the aflatoxins method to look for unreacted B1 or G1 aflatoxins as well as any new peaks not seen before photoreaction. A portion of each sample was also analyzed by mass spectrometry to understand the structure/composition of the reaction products created.

Figure 13:
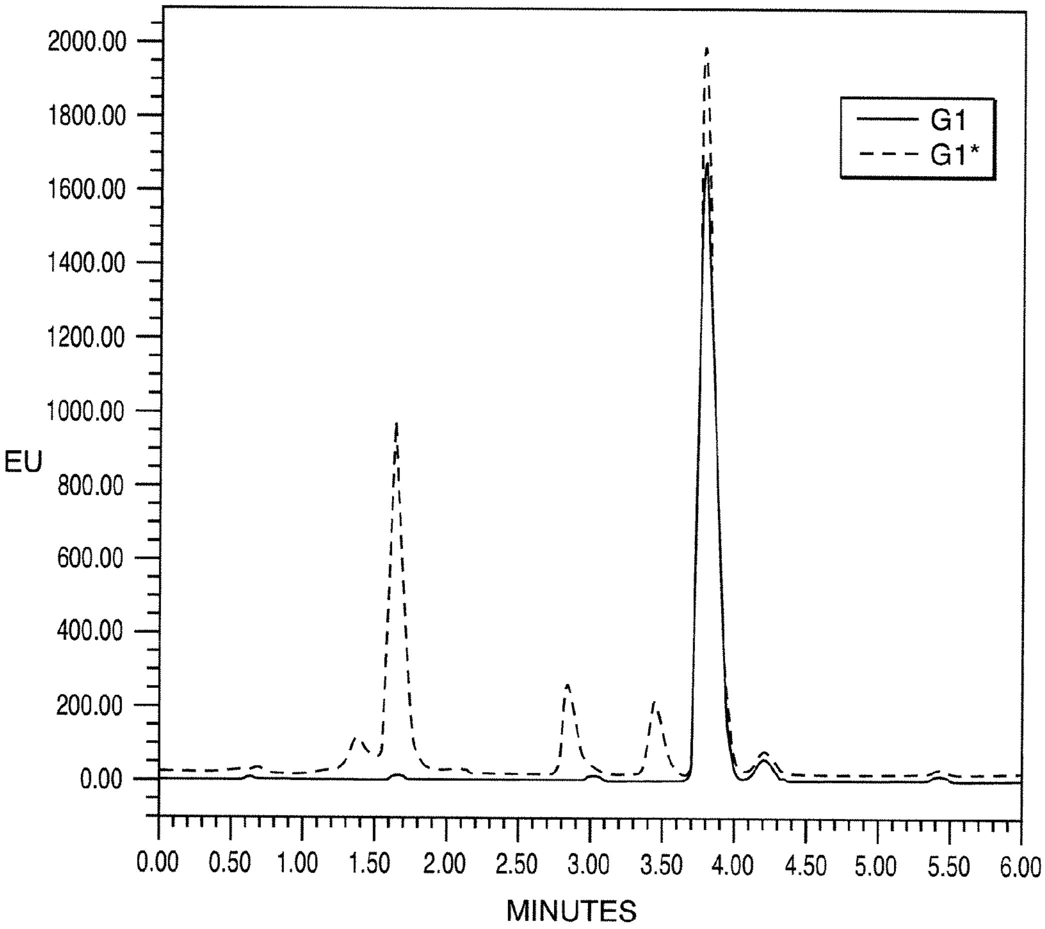
FIG. 13 depicts chromatographs of C1 and photoreacted C1.

A comparison of chromatograms of the G1 standard with photoreacted G1 solution, labeled G1* is shown in FIG. 13. We see both the G1 and G1* samples have the main G1 peak at 3.82 minutes, but the G1* sample also has peaks at 1.37, 1.64, 2.85 and 3.46 minutes. These other peaks are compounds formed in the photoreaction of G1 and the peak at 3.82 minutes is unreacted G1 still present in the sample.

Figure 14:
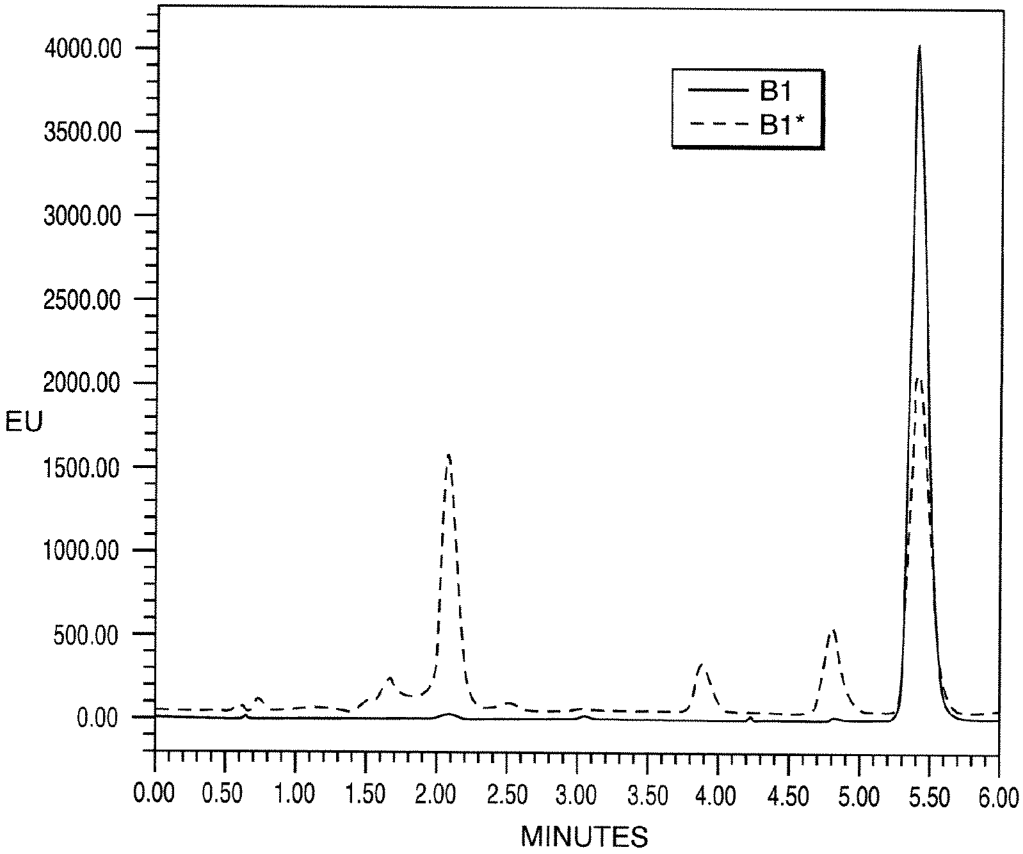
FIG. 14 depicts chromatographs of B1 and photoreacted B1.

Similarly chromatograms of the B1 standard and the photoreacted B1 solution, labeled B1*, are shown in FIG. 14. We see only a single major peak at 5.4 minutes for the B1 standard but the B1* sample has major peaks at 1.65, 2.08, 3.88, 4.80 and 5.4 minutes. These other peaks are compounds formed in the photoreaction of B1 and the peak at 5.4 minutes is unreacted B1.

Mass spectrometry was performed on the same 100 ppb solutions of B1 and G1 and the photoreacted outputs B1* and G1*. The photoreacted samples had mass peaks at +18 and +32 mass units above the parent masses. The +18 is interpreted as water addition and the +32 is interpreted as methanol addition. The chromatograms for the photoreacted samples had more than just two additional peaks. These results show a surprising and unexpected increase in the signal of B1 and G1. Some of the peaks are believed to arise from the water or methanol species being added across the double bond in the furan ring.

Thus, we have described in detail the preferred embodiments of the present invention with the understanding that the invention may be subject to alteration and modification. Therefore, the invention should not be limited to the precise details but should encompass the subject matter of the claims that follow and their equivalents.

The invention claimed is:

1. A method for detecting the presence or absence of one or more aflatoxins potentially present in a sample comprising the steps of providing a device having a vessel, a light source, a source of solution potentially containing photoreactive aflatoxins and a fluorescence detector:

a. the vessel having at least one wall defining a chamber, said chamber capable of performing photoreactions, said chamber defining a chamber volume and having a first window, a second window, an inlet and an outlet, said inlet capable of being placed in fluid communication with a source of solution potentially containing photo-reacting aflatoxin compounds and said outlet capable of discharging products of the photoreaction, said first window capable of being placed in optical communication with a light source to receive photons, said chamber capable of receiving solution over time to define a dwell time and said solution having a concentration of molecules of photo-reacting compounds, said second window capable of emitting photons, wherein prior to introduction of solution into the chamber, the chamber is empty;

b. the light source in optical communication with said first window for emitting photons which photons are received by said first window and transmitted into said chamber, said light source emitting photons at an excitation wavelength selected from the group consisting of approximately 365, 241 and 313 nanometers at a flux of $1.0\times10^{15}$ to $100\times10^{15}$ photons per second;

c. the source of solution potentially containing photo-reacting aflatoxin compounds capable of receiving one or more samples and chromatographically separating the one or more samples into one or more aflatoxin and non-aflatoxin compounds in solution in the event said samples contain an aflatoxin, said source in fluid communication with said inlet of said vessel and capable of placing said solution in said chamber while the chamber is empty with a dwell time of 0.25 to 20.0 seconds per chamber volume;

d. the fluorescence detector in fluid communication with said outlet and capable of detecting the products of the photoreaction, which products are indicative of the presence of aflatoxins and the absence of the products is indicative of the absence of aflatoxins in the sample; and detecting the presence or absence of aflatoxins in said sample using said device.

2. The method of claim 1 wherein said aflatoxin is selected from the group consisting of P1, Q1, M1, B1, G1, B2, and G2.

3. The method of claim 1 wherein said source of solution potentially containing a photo-reacting aflatoxin is a liquid chromatographic column.

* * * * *